US008535264B2

(12) United States Patent
Kirchner

(10) Patent No.: US 8,535,264 B2
(45) Date of Patent: Sep. 17, 2013

(54) DEVICE FOR EXPRESSING MILK

(75) Inventor: Hansjörg Kirchner, Markgröningen (DE)

(73) Assignee: KAWECO GmbH, Ditzingen (DE)

( * ) Notice: Subject to any disclaimer, the term of this patent is extended or adjusted under 35 U.S.C. 154(b) by 509 days.

(21) Appl. No.: 12/224,345

(22) PCT Filed: Feb. 16, 2007

(86) PCT No.: PCT/EP2007/001345
§ 371 (c)(1),
(2), (4) Date: Aug. 25, 2008

(87) PCT Pub. No.: WO2007/098864
PCT Pub. Date: Sep. 7, 2007

(65) Prior Publication Data
US 2009/0024081 A1 Jan. 22, 2009

(30) Foreign Application Priority Data

Mar. 2, 2006 (DE) .......................... 10 2006 009 692

(51) Int. Cl.
*A61M 1/06* (2006.01)
(52) U.S. Cl.
USPC ........................................................... 604/74
(58) Field of Classification Search
USPC ..................................... 604/74–76
See application file for complete search history.

(56) References Cited

U.S. PATENT DOCUMENTS

| 4,964,851 | A | * | 10/1990 | Larsson ............................ 604/74 |
| 5,810,772 | A | * | 9/1998 | Niederberger ................... 604/74 |
| 6,090,065 | A | | 7/2000 | Giles |
| D446,300 | S | | 8/2001 | Kirchner |
| 6,355,012 | B1 | | 3/2002 | Nüesch |
| 7,267,662 | B1 | | 9/2007 | Kirchner |
| 2005/0234400 | A1 | * | 10/2005 | Onuki et al. .................... 604/74 |

FOREIGN PATENT DOCUMENTS

| DE | 38 20 211 C2 | 11/1988 |
| DE | 37 38 282 C2 | 6/1989 |
| DE | 197 00 545 A1 | 7/1998 |
| DE | 102 28 455 A1 | 2/2004 |
| DE | 10228455 A1 * | 2/2004 |
| DE | 10 2004 030 692 B3 | 6/2004 |
| EP | 0 744 180 A2 | 11/1996 |

OTHER PUBLICATIONS

Co-Pending U.S. Appl. No. 11/630,870; inventor Claudia Kirchner; title Milk Extraction Device.

* cited by examiner

*Primary Examiner* — Theodore Stigell
*Assistant Examiner* — Weng Lee
(74) *Attorney, Agent, or Firm* — Pauley Petersen & Erickson

(57) ABSTRACT

A device for expressing milk, with a vacuum-generating unit, which includes a drive motor and a vacuum-generating device, with a switching unit, which is linked to the vacuum-generating unit and determines the suction cycles via a rotatably driven switching member, and with at least one milk expression attachment, which is or can be brought into flow communication therewith and which includes a suction funnel that can be placed on the breast, and a milk collection receptacle. A compact design with reliable function is achieved by the switching member being coupled to the drive motor of the vacuum-generating unit via a transmission for the rotary drive.

14 Claims, 7 Drawing Sheets

DEVICE FOR EXPRESSING MILK

BACKGROUND OF THE INVENTION

1. Field of the Invention

This invention relates to a milk-extraction device with a drive motor and a vacuum generation unit having a vacuum-generating device, a change-over unit attached thereto, which determines the extraction cycles by a rotatingly driven change-over member, and at least one extraction attachment which is or can be brought into a flow connection with it and has a suction funnel, which can be applied to a breast, and a milk receptacle.

2. Discussion of Related Art

A milk-extraction device for human breast milk is disclosed in German Patent Reference DE 102 28 455 B4. In this known milk-extraction device a vacuum generation unit, having a vacuum source or vacuum unit driven by a motor, is connected via a change-over unit, which has a rotating valve and determines the suction cycle to an extraction attachment which has a suction funnel for placement against the breast. For receiving the extracted milk, is a milk receptacle, wherein the milk reaches the latter, secure against flow-back, via a valve arranged at the receptacle opening. For a connection with the vacuum-generation unit on the one hand, and the extraction attachment on the other, openings are in the change-over unit which, for the cyclic generation of the vacuum by rotating channels, can be brought into a flow connection with each other in a rotating change-over member. Also, openings are in the change-over unit which, during the rotation of the change-over unit and the connecting channels contained therein, make a cyclic connection between the extraction attachment and the pressure side of the vacuum unit between the suction phases, so that the extraction effect at the breast is aided, and the actuation of the receptacle valve operates dependably. A cyclical connection with the exterior atmosphere, also provided via the rotating channels, is at a further opening of the change-over unit by an outlet line with a ventilation section and a muffler arranged thereon. Reference is made to the mentioned publication regarding further details of this milk-extraction device, in which regulating possibilities regarding the cycle and/or the strength of the vacuum are also listed. The change-over unit with the rotating valve has proven itself in actual use. However, possibilities still exist for further optimization regarding operation, control and construction.

German Patent Reference DE 10 2004 030 692 B3 discloses a milk-extraction device with two suction attachments, which can be connected to a pump unit 10, wherein a vacuum-generation unit and a change-over unit in accordance with the previously mentioned publication can be contained in the pump unit.

Further milk-extraction devices are shown in German Patent Reference DE 37 38 282 C2, in which a pulsing device is provided for affecting the suction cycle, and U.S. Pat. No. 6,090,065, in which a vacuum-generation device with diaphragm elements arranged in a special way and channel arrangements are provided.

A further milk-extraction device is shown in German Patent Reference DE 38 20 211 C2, in which a fluid-collecting vessel is connected via a valve arrangement with a vacuum source or with the atmosphere, and a cyclical change between suction and airing phases is controlled by a timed switching arrangement. A valve arrangement is actuated by a magnetic coil.

SUMMARY OF THE INVENTION

One object of this invention is to provide a milk-extraction device of the type mentioned above but in which dependable functioning is achieved, along with a compact structure.

This object is attained by a milk extraction device having characteristics taught in the claims and this specification. For being rotatorily driven, the change-over member is coupled via a gear train with the drive motor of the vacuum generation unit.

With these steps the drive of the vacuum generation device is also used for the change-over unit, with which a compact construction is achieved, along with a compact construction, and advantageous uses also result with respect to operation and handling.

In one embodiment, with respect to function and construction, the gear train is designed as an adjusting unit for the mechanical, continuous setting of the number of revolutions, or at least a stepped two-stage setting of a differing number of revolutions, of the change-over member. The gear train has a drive worm gear seated in the extension of, or parallel to, a motor shaft of the drive motor, which drives a first toothed disk. The first toothed disk which is orthogonally seated in relation to the motor shaft, can be brought into engagement by an axial displacement with at least two further toothed disks with a number of teeth different from each other and which determine the stepping of the number of revolutions of the change-over member.

The steps, wherein the further toothed disks are concentrically seated on a common shaft, can be axially shifted in relation to the shaft and can be brought relatively to it into fixed engagement in the circumferential direction, in which the change-over member is also seated in fixed engagement in the circumferential direction relative to the shaft, to provide a compact construction and dependable functioning.

The cyclic flow conditions, along with dependable functioning, are aided because the change-over member is provided with at least one bridging channel, by which an alternating connection between the extraction attachment on the one side and a vacuum pump device on the other side can be established.

Also, advantages regarding the construction and mode of functioning result if the rotatingly driven change-over member is designed flat on at least one side, and with this side sufficiently covers openings arranged on a facing, also flat designed stationary section on the opening side of the change-over unit for assuring a sufficient vacuum effect and overpressure effect. For producing the alternating connection of the extraction attachment with the vacuum side and the overpressure side of the vacuum generation unit, connecting openings of the at least one bridging channel are arranged, which can be cyclically brought into flow connection with openings of the stationary section, which are to be respectively assigned to them.

Advantageous setting possibilities are obtained if the change-over unit has an actuating lever, which can be manually operated, with which the relative displacement of the at least two further toothed disks with respect to the first toothed disk can be performed.

Here, functioning and handling are eased because the actuating lever is seated on the shaft so it can be rotated relatively to it and has an at least partially circumferential tilted adjustment section, by which the axial displacement of the two further toothed disks can be provided via at least one possibly provided intermediate piece.

Advantages regarding construction and functioning are further obtained if, for operating the vacuum pump device, a crankshaft is arranged in the drive train, to which a vacuum pump unit is coupled by at least one intermediate member connected to it.

The steps, wherein at least two vacuum pump units are placed, axially offset, opposite each other at identical angular distances around the crankshaft, also contribute to a dependable mode of operation, because their suction and pressure forces are distributed during rotation.

In this case further advantages, for example regarding a freedom from vibration, result if the vacuum pump units are coupled to the crankshaft so that they simultaneously generate suction on the one hand, and simultaneously pressure with respect to each other.

The use of the milk-extraction device is improved if more than one extraction attachment is connected to the change-over unit.

BRIEF DESCRIPTION OF THE DRAWINGS

This invention is explained in greater detail in view of exemplary embodiments, making reference to the drawings, wherein.

DETAILED DESCRIPTION OF THE INVENTION

Figures 1, 2:
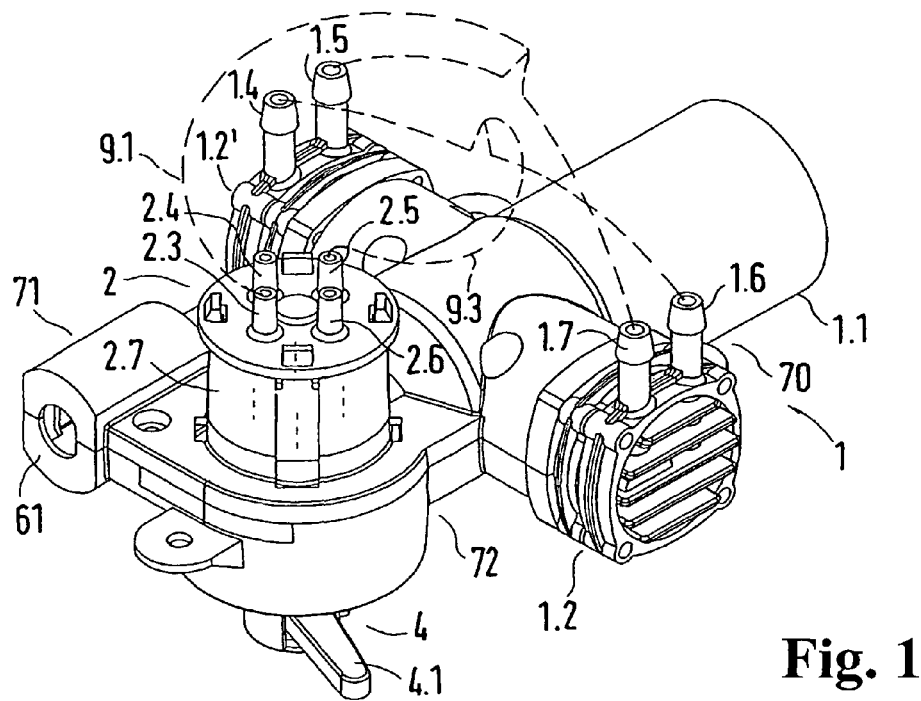
FIG. 1 is a unit having the vacuum generation device and the change-over unit, in a perspective view.
FIG. 2 is a schematic representation of a milk-extraction device with a vacuum generation device and change-over unit, as well as an extraction arrangement.

A portion of the milk-extraction device is represented in FIG. 1, in which a vacuum generation unit 1 with a drive motor 1.1 and two oppositely arranged vacuum pump units 1.2, 1.2' are combined, together with a change-over unit 2, in a common housing 70 having a housing base 71 and a housing top 72. Respectively, two pump unit connectors 1.4, 1.5 or 1.6, 1.7 are provided at the vacuum pump units 1.2, 1.2', one side of which is in a flow connection with the vacuum side and the other side with the pressure side of the vacuum pump units 1.2, 1.2'. The change-over unit 2 is partially received in a cylinder-shaped housing section 2.7, which is covered on its top by a cover element 2.8 which is maintained on the cylinder-shaped housing section 2.7 by snap-in fingers 2.71. First, second, third and fourth openings 2.3, 2.4, 2.5, 2.7 with respective connecting sleeves are arranged in the cover element 2.8, of which the first and third openings 2.3 or 2.5 are connected by an underpressure line 9.1 or by an overpressure line 9.3 with the vacuum side or with the pressure side of vacuum pump unit 1.1, 1.2', wherein the two pressure sides of the vacuum pump units 1.2, 1.2' are connected by a Y-piece with the underpressure line 9.1 or the overpressure line 9.3.

Figure 5:
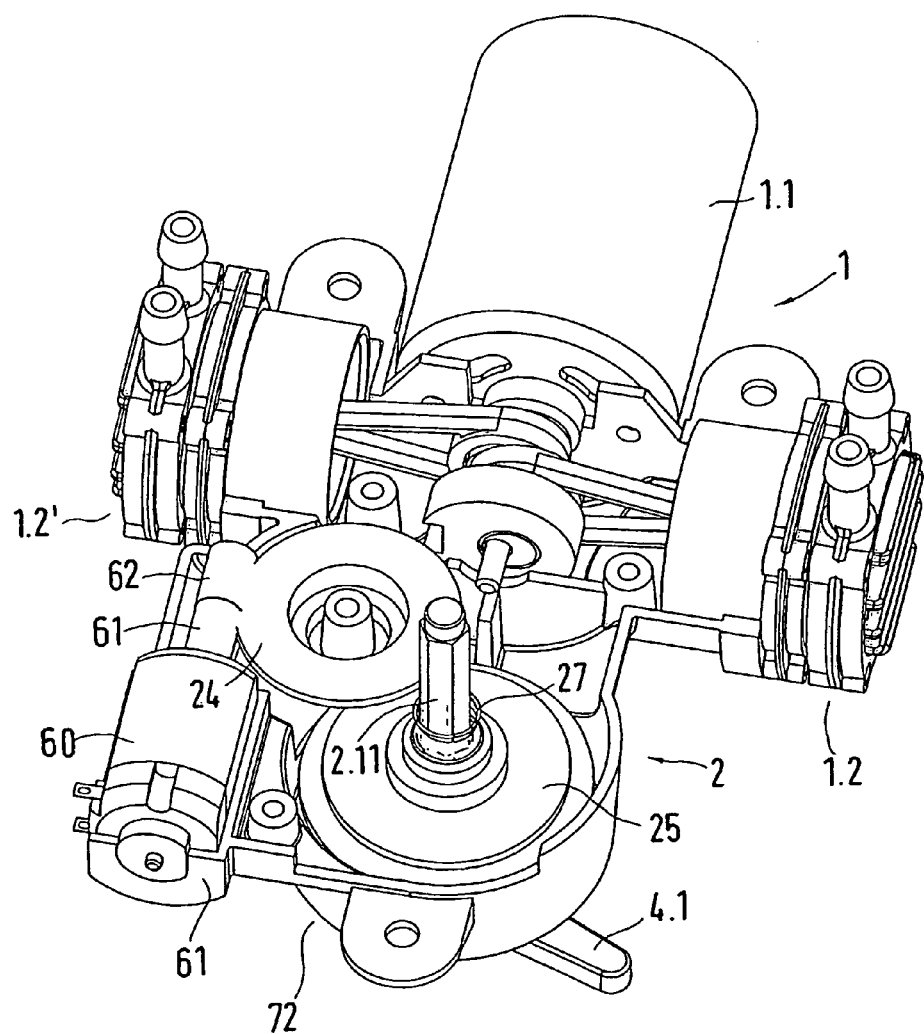
FIG. 5 shows a further perspective representation of the unit in accordance with FIG. 1 in the opened state.

FIG. 1 shows a supplementary motor housing element 61, in which a supplementary motor 60, as shown in FIG. 5, can be housed as an alternative drive mechanism for the change-over unit 2.

FIG. 2 shows the connection of the unit including the vacuum generation unit 1 and the change-over unit 2 represented in FIG. 1 with an extraction attachment 10 via a connecting line 9.2, and with a further extraction attachment 10' via a further connecting line 9.4. Each of the extraction attachments 10 or 10' has a suction funnel 6 for placement against the breast and a receptacle 7 for storing the extracted milk, connected with it via a conduit, wherein an inlet valve 8 is provided in the inlet area of the receptacle 7, which prevents a return flow of milk and also contributes to the creation of a defined vacuum in the extraction attachment 10, 10' at the breast. The vacuum in the suction funnel 6 can be regulated, preferably manually, by an auxiliary air regulating device 5. With the aid of a manually operable actuating lever 4.1 the suction cycle can be varied by an adjusting unit 4 represented in FIG. 1 so that the number of revolutions of a change-over member 2.10, which is rotatorily driven in the change-over unit 2, is placed between different settings a), b) into at least two stages, or alternatively is set to continuous operation. For rotatory driving, the change-over member 2.10 is connected via a gear train 20 with the drive motor 1.1 of the vacuum generation unit 1, with which the vacuum pump units 1.2, 1.2' are also driven. A further regulating device 5' can be provided in the underpressure line 9.1, for example, for the further regulation of the vacuum generation. Reference is made to the German Patent Reference DE 102 28 455 B4 mentioned with respect to more detailed information regarding the functioning of the change-over unit 2 with the rotating change-over member 2.10 and the alternating connection of the vacuum source or vacuum side on the one hand and the pressure source or pressure side on the other, of the vacuum generation unit 1 with the extraction arrangement 10. The alternating charging with vacuum and compressed air of the further extraction arrangement 10' takes place correspondingly via the further connecting line 9.4.

Figure 3:
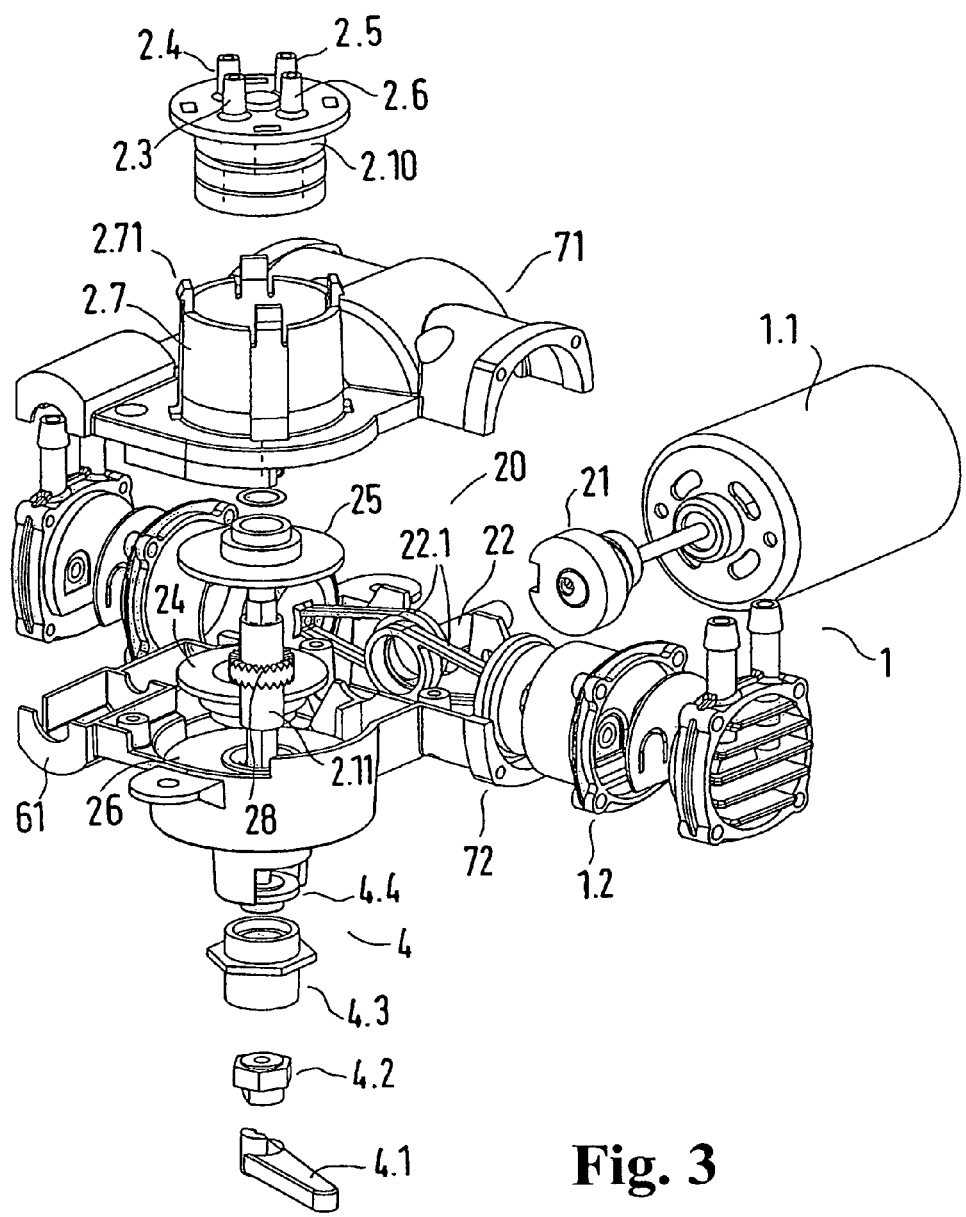
FIG. 3 shows the unit represented in FIG. 1 in an exploded perspective representation.

The exploded representation in accordance with FIG. 3 shows the interior components of the unit including the vacuum generation unit 1 and change-over unit 2. With a drive coupling element 21, the drive motor 1.1 is connected via a motor shaft to a crankshaft 22, at whose crank sections coupling elements in the shape of connecting rods 22.1 are seated, by which the vacuum pump units 1.2, 1.2' are driven by the respective back and forth movement of pump pistons or diaphragms for generating the vacuum on the one side and the pressure on the other side. This drive mechanism of the vacuum pump units 1.2, 1.2' operates in accordance with the principle of a boxer motor. Other coupling elements, which are put eccentrically into motion, can also be provided in place of the connecting rods 22.1.

Figure 4:
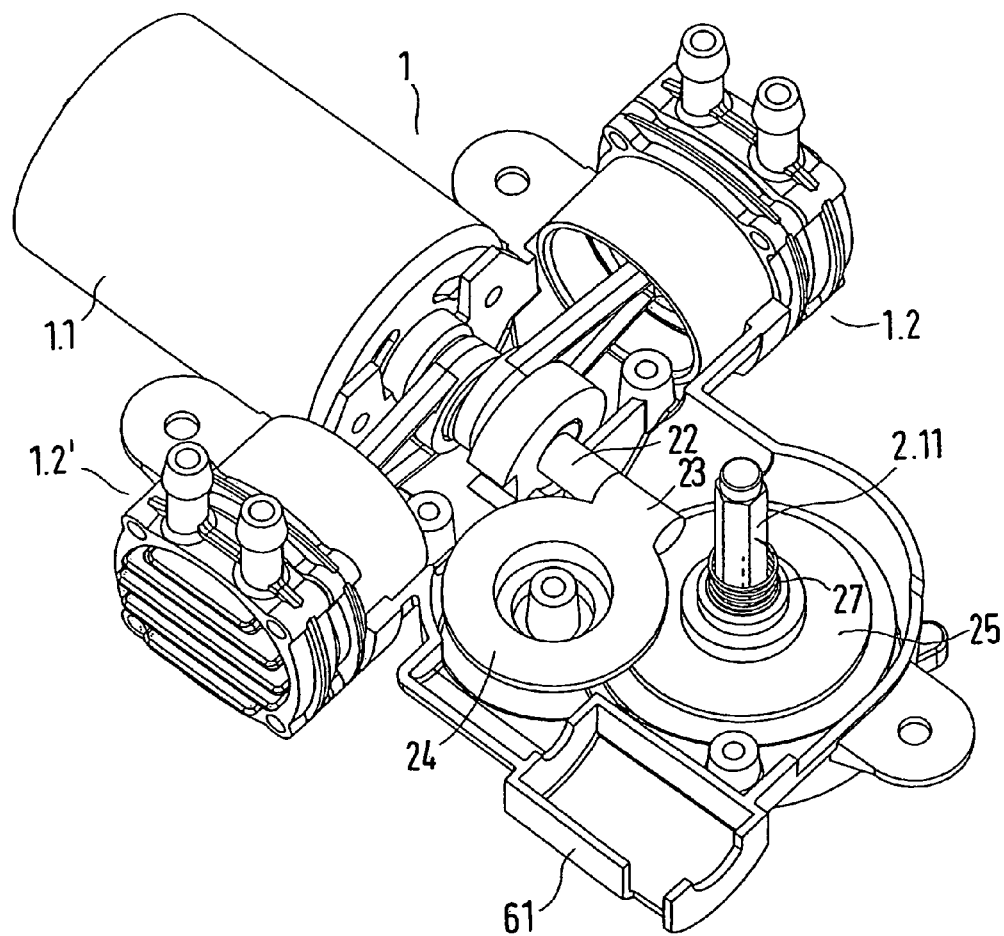
FIG. 4 shows the unit represented in FIG. 1 but in an opened state in an expanded perspective representation.
Figure 6B:
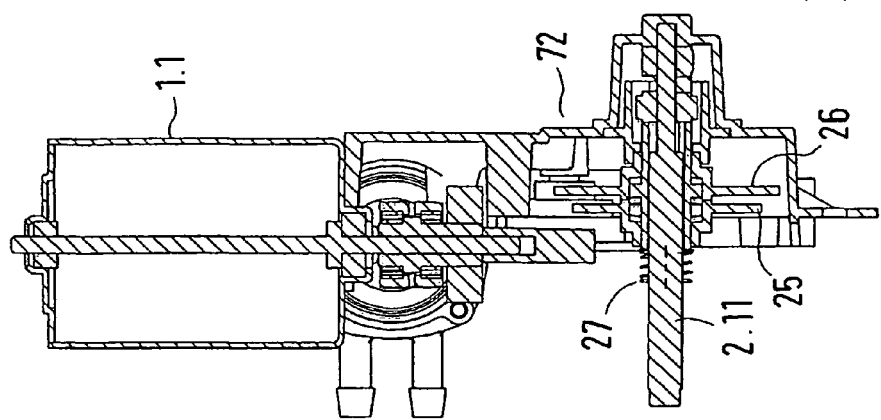
FIGS. 6A and 6B each shows a view from above on the unit in accordance with FIG. 1 in a partially opened state, as well as in longitudinal section along a section plane A-A.
Figure 6A:
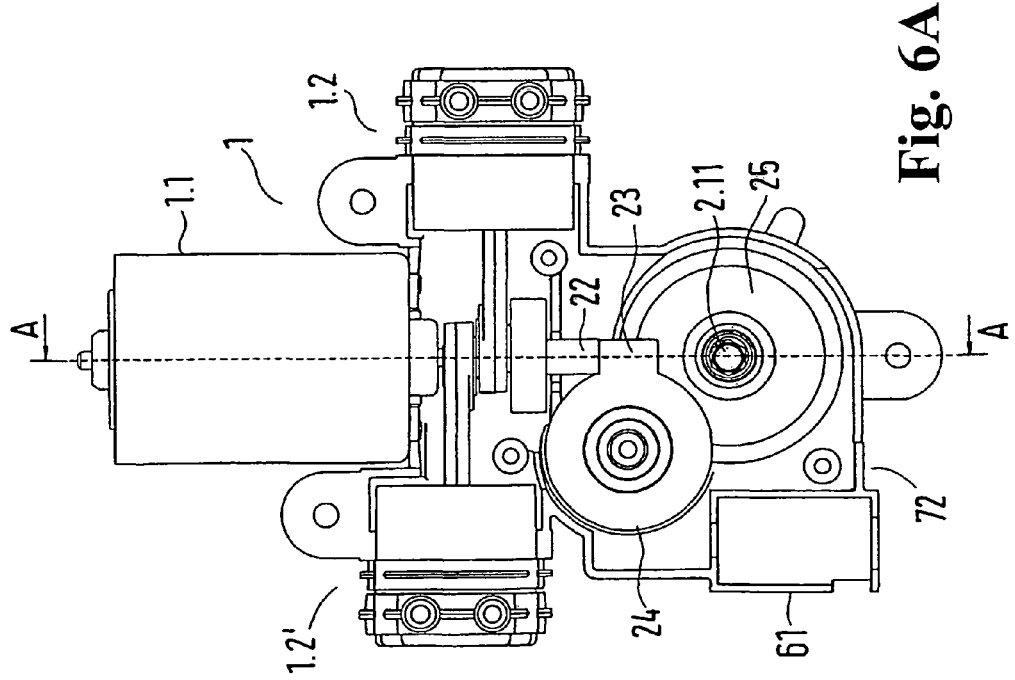
Figure 7A:
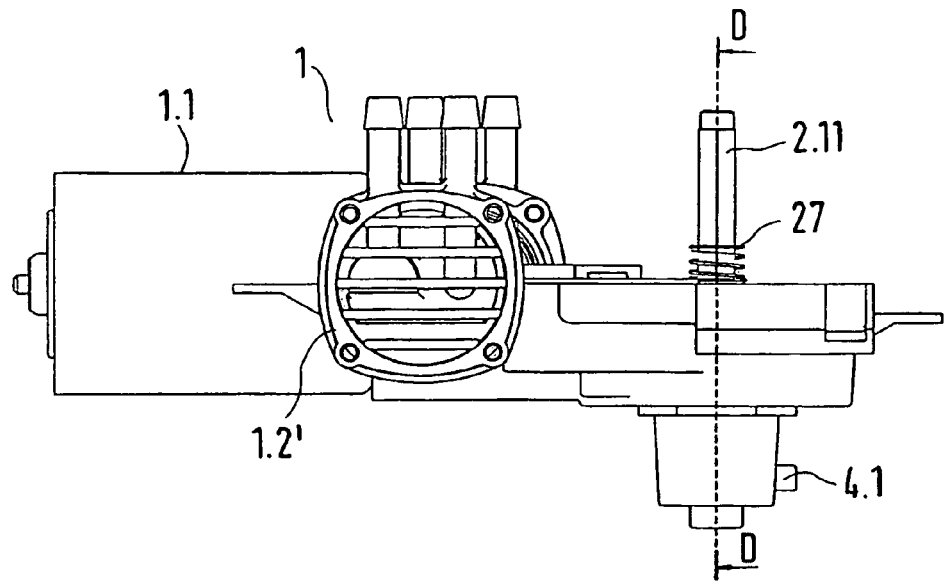
FIGS. 7A and 7B each shows a lateral view on the unit in accordance with FIG. 1 in a partially opened state and a cross section along a section line D-D.
Figure 7B:
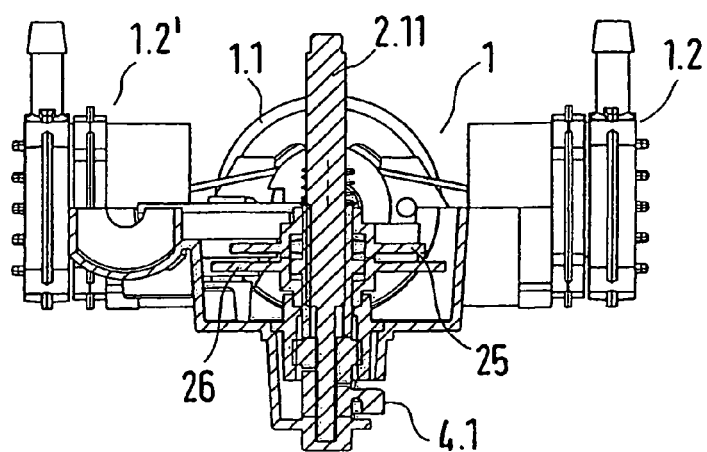

As shown in connection with FIGS. 4, as well as FIGS. 6A, 6B, in the extension of the crankshaft 22 a worm drive 23 which is schematically represented is arranged on the drive train 20 at the end section of the crankshaft 22, which works together with a first toothed disk 24, also schematically represented, for putting the latter into rotation. The axis of rotation of the first toothed disk 24 is arranged orthogonally with respect to the axis of the crankshaft, or motor shaft, is offset parallel, if required, and has, as FIGS. 6B and 7B show, two further gear rims of different diameter, which can be brought into engagement with a second toothed disk 25, or third toothed disk 26, and are in engagement with one of these two toothed disks as a function of the switched position. The second and the third toothed disks 25 or 26 are also seated, axially displaceable, on a shaft 2.11 of the change-over unit 2 arranged orthogonally with respect to the axis of the crankshaft 22, or motor shaft, wherein as a result of the axial displacement either the second toothed disk or the third toothed disk comes into engagement with a toothed member 28, which is seated, fixed against relative rotation, on the shaft 2.11, namely the one which has also been put into engagement with the first toothed disk 24. In order to come into engagement with the toothed member 28, particularly with its upper tooth arrangement or its lower tooth arrangement, the second and third toothed wheels 25, 26 have appropriately matched tooth arrangements in the interior area, such as FIG. 3 shows for the third toothed disk 26. The respective second or third toothed disks 25, 24 not in engagement with the first toothed disk 24 are also not in engagement with the toothed member 28. Thus the shaft 2.11 is rotatingly driven at the respective number of revolutions either via the second toothed disk 25 or the third toothed disk 26. The gear for driving the change-over member 2.10 thus corresponds in principle to a Hirth gear, or also a planetary gear. The change-over member 2.10 is seated on the upper section shaft 2.11, fixed against relative rotation with respect to it, and has bow-shaped bridging paths 2.1, 2.2, such as shown in FIG. 2, in order to bring the two extraction attachments 10, 10' alternatingly into contact with the vacuum and the pressure side of the vacuum pump unit 1.2, 1.2' via the pump unit connectors 1.4, 1.5, 1.6, 1.7, as well as the first, second, third and fourth openings 2.3, 2.4. 2.5, 2.6 and the respective lines 9.1, 9.2, 9.3, 9.4.

A circumferential inclined adjustment device, by which the second and third toothed disks 25, 26 are displaced by several intermediate pieces 4.2, 4.3, 4.4 and an inclined counter-adjustment device, are arranged on the actuating lever 4.1, which is rotatably seated in the lower area of the shaft 2.11 and is axially immovably maintained in the housing base 71, for the axial displacement of the second and third toothed disk 25, 26 on the shaft 2.11. A counter-force is exerted from above on the toothed disks 25, 26 by an actuating spring 27, by which the toothed disks 25, 26 are displaced in the opposite direction after returning the actuating lever 4.1.

Figure 8A:
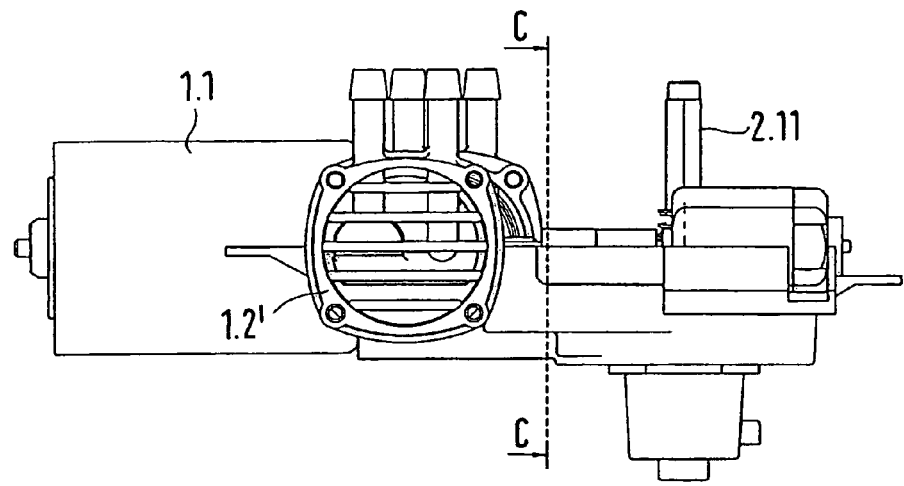
FIGS. 8A and 8B each shows a further lateral representation of the unit in accordance with FIG. 1 in a partially opened state, with a supplementary motor, and a sectional representation along a section plane C-C.
Figure 8B:
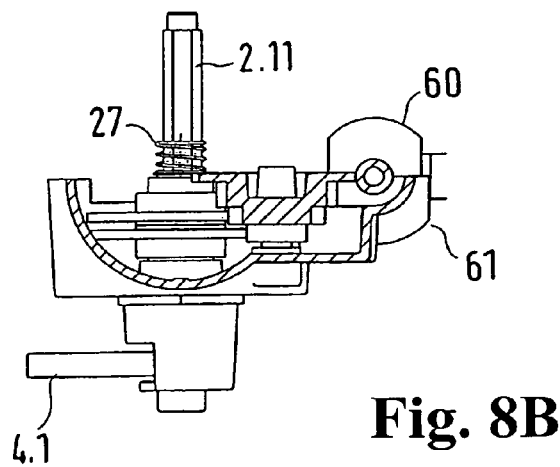

In place of driving by the drive motor 1.1 by the gear train 20, in an alternative embodiment the drive of the change-over member 2.1 takes place via the supplementary motor 60, as shown in FIGS. 5 and 8A, 8B. In this case, the motor shaft of the supplementary motor 60 drives the first toothed disk 24 via a further worm gear 62, and also causes the driving of the shaft 2.11 via the second and third toothed disk 25, 26, and thus of the change-over member 2.10, as described above.

The invention claimed is:

1. A milk-extraction device with a drive motor (1.1) and a vacuum generation unit (1) having a vacuum-generating device (1.2, 1.2'), a change-over unit (2) attached via pressure lines to the vacuum-generating device (1.2, 1.2') including a rotational valve having a rotatingly driven change-over member (2.10) which determines extraction cycles, and at least one extraction attachment (10, 10') which is brought into a flow connection with the change-over unit (2) and having a suction funnel (6) which can be applied to a breast, and a milk receptacle (7), the milk-extraction device comprising:
for being rotatorily driven, the change-over member (2.10) coupled via a gear train (20) with the drive motor (1.1) of the vacuum generation unit (1), the gear train (20) having a drive worm gear (23) seated in an extension of or parallel to a motor shaft of the drive motor (1.1) which drives a first toothed disk (24), and the first toothed disk (24) is orthogonally seated relative to the motor shaft and is engageable by an axial displacement with at least two further toothed disks (25, 26) with a number of teeth different from each other, which determine a stepping of a number of revolutions of the change-over member (2.10), wherein the gear train (20) is designed as an adjusting unit (4) for a mechanical continuous setting of a number of revolutions of the rotatingly driven change-over member (2.10) of the rotational valve, or at least a stepped two-stage setting of a differing number of revolutions of the change-over member (2.10), wherein for operating the vacuum generation unit, a crankshaft (22) is arranged in the gear train (20), to which at least two vacuum-generating devices (1.2, 1.2') are coupled by at least a respective one connected intermediate member (22.1), and wherein the at least two vacuum-generating devices (1.2, 1.2') are axially offset opposite each other at identical angular distances around the crankshaft (22).

2. The milk-extraction device in accordance with claim 1, wherein the further toothed disks (25, 26) are concentrically seated on a common shaft (2.11) and are axially shifted relative to the shaft and can be brought into fixed engagement in a circumferential direction, in which the change-over member (2.10) is seated in fixed engagement in the circumferential direction relative to the shaft.

3. The milk-extraction device in accordance with claim 2, wherein the change-over member (2.10) has at least one bridging channel (2.1, 2.2) by which an alternating connection between the extraction attachment (10) on the one side and a vacuum pump device (1.2, 1.2') on a vacuum side, or an overpressure side (1.3) on an other side is established.

4. The milk-extraction device in accordance with claim 3, wherein the rotatingly driven change-over member (2.10) is flat on at least one side—that sufficiently covers openings (2.3, 2.4, 2.5, 2.6) arranged on a facing, and a flat stationary section on an opening side of the change-over unit (2) assures a sufficient vacuum effect and overpressure effect, and for producing an alternating connection of the extraction attachment (10) with the vacuum side (1.2, 1.2') and the overpressure side (1.3) of the vacuum generation unit (1), connecting openings of the at least one bridging channel (2.1, 2.2) can be cyclically brought into flow connection with the openings (2.3, 2.4, 2.5, 2.6) of the stationary section respectively assigned to them.

5. The milk-extraction device in accordance with claim 4, wherein the change-over unit (4) has an actuating lever (4.1) manually operable with which occurs a relative displacement of the at least two further toothed disks (25, 26) with respect to the first toothed disk (24).

6. The milk-extraction device in accordance with claim 5, wherein the actuating lever (4.1) is seated on a shaft (2.11) for relative rotation and has an at least partially circumferential tilted adjustment section for axial displacement of the two further toothed disks (24, 25) via at least one intermediate piece (4.2, 4.3, 4.4).

7. The milk-extraction device in accordance with claim 6, wherein the vacuum pump units (1.2, 1.2') are coupled to the crankshaft (22) to simultaneously generate suction and pressure with respect to each other.

8. The milk-extraction device in accordance with claim 1, wherein the change-over member (2.10) has at least one bridging channel (2.1, 2.2) by which an alternating connection between the extraction attachment (10) on the one side and a vacuum pump device (1.2, 1.2') on a vacuum side, or an overpressure side (1.3) on an other side is established.

9. The milk-extraction device in accordance with claim 8, wherein the rotatingly driven change-over member (2.10) is flat on at least one side that sufficiently covers openings (2.3, 2.4, 2.5, 2.6) arranged on a facing, and a flat stationary section on an opening side of the change-over unit (2) assures a sufficient vacuum effect and overpressure effect, and for producing an alternating connection of the extraction attachment (10) with the vacuum side (1.2, 1.2') and the overpressure side (1.3) of the vacuum generation unit (1), connecting openings of the at least one bridging channel (2.1, 2.2) can be cyclically brought into flow connection with the openings (2.3, 2.4, 2.5, 2.6) of the stationary section respectively assigned to them.

10. The milk-extraction device in accordance with claim 1, wherein the change-over unit (4) has an actuating lever (4.1) manually operable with which occurs a relative displacement of the at least two further toothed disks (25, 26) with respect to the first toothed disk (24).

11. The milk-extraction device in accordance with claim 10, wherein the actuating lever (4.1) is seated on a shaft (2.11) for relative rotation and has an at least partially circumferential tilted adjustment section for axial displacement of the two further toothed disks (24, 25) via at least one intermediate piece (4.2, 4.3, 4.4).

12. The milk-extraction device in accordance with claim 1, wherein the vacuum pump units (1.2, 1.2') are coupled to the crankshaft (22) to simultaneously generate suction and pressure with respect to each other.

13. The milk-extraction device in accordance with claim 1, wherein more than one extraction attachment (10, 10') is connected to the change-over unit (2).

14. A milk-extraction device, comprising:
- a vacuum generation unit (1) including a drive motor (1.1) connected to a vacuum-generating device (1.2, 1.2');
- a change-over unit (2) including a plurality of openings and a rotational valve having a rotatingly driven change-over member (2.10) that determines extraction cycles, a first opening of the plurality of openings connected by an underpressure line to the vacuum-generating device (1.2, 1.2'), and a second opening of the plurality of openings connected by an overpressure line to the vacuum-generating device (1.2, 1.2');
- a gear train coupling the change-over member (2.10) with the drive motor (1.1) and providing rotational drive for the rotatingly driven change-over member (2.10), wherein the gear train (20) is designed as an adjusting unit (4) for a mechanical continuous setting of a number of revolutions of the rotatingly driven change-over member (2.10) of the rotational valve, or at least a stepped two-stage setting of a differing number of revolutions of the change-over member (2.10), the gear train (20) including a drive worm gear (23) seated in an extension of or parallel to a motor shaft of the drive motor (1.1), which drives a first toothed disk (24), and the first toothed disk (24) is orthogonally seated relative to a motor shaft and engageable by an axial displacement with at least two further toothed disks (25, 26) with a number of teeth different from each other, which determine a stepping of a number of revolutions of the change-over member (2.10);
- at least one extraction attachment (10, 10') including a suction funnel (6) which can be applied to a breast, and a milk receptacle (7), wherein the extraction attachment (10, 10') is connectable in a flow connection with a third opening of the plurality of openings of the change-over unit (2);
- a crankshaft (22) is arranged in the gear train (20) for operating the vacuum generation unit (1), to which at least two vacuum-generating devices (1.2, 1.2') are coupled by at least a respective one connected intermediate member (22.1) and wherein the at least two vacuum-generating devices (1.2, 1.2') are axially offset opposite each other at identical angular distances around the crankshaft (22).

* * * * *